US006307113B1

(12) United States Patent
Sabahi

(10) Patent No.: US 6,307,113 B1
(45) Date of Patent: Oct. 23, 2001

(54) SELECTIVE BROMINATION OF AROMATIC COMPOUNDS

(75) Inventor: Mahmood Sabahi, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 09/647,502

(22) PCT Filed: Mar. 26, 1999

(86) PCT No.: PCT/US99/06456

§ 371 Date: Sep. 27, 2000

§ 102(e) Date: Sep. 27, 2000

(87) PCT Pub. No.: WO99/50206

PCT Pub. Date: Oct. 7, 1999

(51) Int. Cl.[7] .................................................... C07C 22/00
(52) U.S. Cl. ........................................... 570/147; 570/206
(58) Field of Search ................................. 570/206, 207, 570/210, 147

(56) References Cited

U.S. PATENT DOCUMENTS 3,518,316    6/1970    Cumbo .

FOREIGN PATENT DOCUMENTS 0492594     7/1992    (EP) .
0761627A  *  3/1997    (EP) .
2221640     9/1987    (JP) .
6314742     1/1988    (JP) .

OTHER PUBLICATIONS

Ratnasamy, et al., "Halogenation Over Zeolite Catalysts", Applied Catalysis A: General 135, 1996, pp. 25–55.
Clark, et al., "Environmentally friendly catalysis using supported reagents: the fast and selective bromination of aromatic substrates using supported zinc bromide", Chem. Commun., 1997, pp. 1203–1204.
Clark, et al., "Environmentally Friendly Catalytic Methods", Chemical Society Reviews, 1996, pp. 303–310.
de la Vega, et al., "Selective liquid–phase bromination of toluene catalysed by zeolites", Zeolites, 1989, vol. 9, Sep., pp. 418–422.
de la Vega, et al., "Selective para–Bromination of Toluene Catalysed by Na–Y Zeolite in the Presence of an Epoxide", J.Chem.Commun.,1989, pp. 653–654.

* cited by examiner

Primary Examiner—Alan Siegel
(74) Attorney, Agent, or Firm—E. E. Spielman, Jr.

(57) ABSTRACT

Aromatic substrates such as fluorobenzene can be selectively brominated in high yield and conversion in short reaction periods by reacting the substrate with a brominating agent in a liquid reaction medium and in the presence of a catalyst composition formed by including in the medium a combination of (i) a shape selective HY or HM or zeolite catalyst, and (ii) at least one Lewis acid in a ratio of from 0.005 to 0.5 part by weight of (ii) per part by weight of (i). The bromination is performed at one or more temperatures in the range of 30 to 70° C., and the amount of the zeolite is no more than about 10 grams per mole of aromatic substrate.

20 Claims, No Drawings

SELECTIVE BROMINATION OF AROMATIC COMPOUNDS

REFERENCE TO RELATED APPLICATIONS

This is the National Stage of International Application Number PCT/US99/06456, filed Mar. 26, 1999, and which is a continuation-in-part of commonly-owned prior U.S. application Ser. No. 09/049,189, filed Mar. 27, 1998, now abandoned.

TECHNICAL FIELD

This invention relates to the selective aromatic bromination (ar-bromination) of aromatic substrates, and more specifically to an improved process for the selective para-bromination of benzene derivatives in the presence of a shape selective zeolite catalyst.

BACKGROUND

The selective para-bromination of toluene, catalyzed by NaY zeolite in the presence of an epoxide, has been reported by F. de la Vega et al., *J Chem. Soc., Chem. Commun.*, 1989, 653. The ratio of p- and o-isomers obtained was 98 to 2, but only about 10 to 13 percent of the toluene was converted. In experiments using no epoxide or in the presence of carbonates, the reaction proceeded to completion but the final para-selectivity was only 67%. The amount of zeolite catalyst used was about 0.09 gram per mmol of toluene. It was stated that adding a fresh batch of catalyst made the reaction resume with the same selectivity, but the final conversions obtained are not reported.

The para-selective bromination of benzene derivatives, such as toluene, using shape-selective zeolite catalysts, for example, NaY, HY, and NaX zeolites, has also been described by K. Smith et al., "Highly efficient para-selective bromination of simple aromatic substrates by means of bromine and a reusable zeolite," *Chem. Commun.*, 1996, 467–468. In contrast to de la Vega, much larger amounts of zeolite were used in order to obtain complete conversion. When NaY zeolite was used in an amount of 0.55 gram per 0.85 mmol of toluene (0.65 gram per mmol), it was reported that 98% absolute yields of p-bromotoluene were obtained. When the reaction was carried out with fluorobenzene and NaY zeolite, only 92% of the desired p-bromofluorobenzene was obtained. The yield of para-brominated products which can be achieved is also indicated to depend upon the type of zeolite used. For example, NaY zeolite gave better conversion (yield) than using the same amount of a NaX zeolite in producing p-bromotoluene. Smith et al. claim that the zeolite catalysts can be regenerated by calcination, but it is not believed that calcination returns the zeolites to their original state. The selectivity incorporated by zeolite in the Smith et al. process does not offer any economical advantage over the available commercial methods (which can produce up to 90% of the desired p-bromofluorobenzene) for the following reasons:

1) Use of a very dilute reaction medium (about 1 wt % of the total reaction mixture) decreases plant throughput;
2) A huge excess of zeolite is used (7 wt %, or a seven-fold excess over the substrate); and
3) Low selectivity for the para-isomer is shown; para/ortho (p/o)=92/8. In any event, the relatively large amount of catalyst required to be regenerated would make this process too expensive to be practical from a commercial standpoint.

Fluorobenzene is a deactivated system towards electrophilic aromatic substitution and requires Lewis acid catalysis for the improvement of the rate of the substitution reaction. However, strong Lewis acid catalysts create fast reactions with lower p/o ratios. Control of the reaction rate with catalyst and temperature are two methods reported for the improved selectivity. For example, Jacob Oren in EP 0 761 627 A1 describes the effect of temperature on the para-selectivity of the reaction of fluorobenzene with bromine. Selectivities as high as 97–98% were reported at temperatures between 0 to −20° C., and even higher selectivities were achieved at temperatures between −17 and −65° C. Use of such low temperature operations is not a preferred way of operating on a commercial basis.

It would be highly advantageous if a way could be found to produce bromoaromatic compounds in high yield and selectivity by process technology suitable for use on an industrial scale, while at the same time utilizing a shape-selective zeolite catalyst more efficiently than the processes described in the foregoing literature references. In the case of p-bromofluorobenzene production, such process technology would be particularly attractive if product with para/ortho ratios in the vicinity of 98/2 could be achieved without need for any operations conducted at temperatures below room temperature (i.e., below ca. 20° C.). This invention is deemed to fulfill this objective most expeditiously.

SUMMARY OF THE INVENTION

In accordance with one embodiment of this invention, there is provided a process for selectively ar-brominating an aromatic substrate. The process comprises reacting said substrate with bromine in a liquid reaction medium and in the presence of a catalyst composition formed by including in the reaction medium (i) a shape selective HY or HMor zeolite catalyst, and (ii) at least one Lewis acid, typically in a ratio of from 0.005 to 0.5 part by weight of (ii) per part by weight of (i). The amount of such zeolite catalyst is no more than about 10 grams per mole of the aromatic substrate, and thus at most is less than one-fifth of the amount of zeolite described in the above publication of Smith et al. The reaction temperature in the present process is kept between 30° C. and 70° C., and most preferably between 35° C. and 50° C., throughout substantially the entire reaction period.

Among the major advantages achievable by the practice of this invention in the proper manner include (a) higher p/o selectivity, (b) faster conversion rate, and (c) lower cycle times as compared to use of the same amount of HY or HMor zeolite or a metal-containing Lewis acid as the sole catalyst component.

These and other embodiments of this invention will be still further apparent from the ensuing description and appended claims.

Zeolites

With reference to zeolites in general, the aluminum atom in the framework of the aluminosilicate zeolites carries a negative charge which is associated with a cation such as sodium, or a proton, the latter case being the source of the Bronsted acidity of the zeolite. Different families of zeolites provide dramatically different pore structures and sizes. Faujasites (Y zeolites) have intersecting channels with pore size of 7.0–7.4 Å. Mordenites have one-dimensional channels and pore sizes of 6.7–6.8 Å. Within each family, zeolites with varying Si/Al ratios have been synthesized.

The HY and HMor zeolite catalysts for use in the process of the invention are chosen such that the aromatic substrate will fit into the pores of the zeolite. This permits bromination to occur within the pores where access to sites on the substrate other than the desired position is hindered. Accordingly, such zeolite catalysts are termed as being "shape selective." For simple mononuclear aromatic compounds such as, toluene, fluorobenzene, and isobutylbenzene, HY zeolites which have a pore (aperture) size of about 7 angstroms give para-brominations in high yield and selectivity provided the zeolites are dried and kept dry. The optimum pore size for the selective bromination of other aromatic substrates is selected depending upon the size and shape of the molecules to be brominated. In general, the pore size should range from 6 to 8 angstroms and preferably from 6.5 to 7.5 angstroms. It is conceivable that by changing temperature, solvent, cation, etc., it may become practical to carry the process with zeolites which have smaller aperture sizes. Suitable HY and HMor zeolites for use in the practice of this invention are available as articles of commerce. For example, suitable HY zeolites are available from Tosoh USA, Inc. as zeolites 320HOA, 360HUA, and 390HUA. Likewise zeolites HSZ-620HOA, HSZ-640HOA, and HSZ-690HOA are examples of HMor zeolites available from Tosoh USA, Inc. that are suitable for use in the practice of this invention.

The pores of the zeolite particles, where the selective bromination process takes place, should be kept substantially free of absorbed water. Accordingly, in practicing the process of the invention, the zeolites should have an absorbed water content of no greater than about 7.5 weight percent, preferably no greater than about 5.0 weight percent, and most preferably less than 5 weight percent water, based on the total weight of zeolite and water. As used in the specification and claims herein, by "absorbed water content" is meant the weight percent of water which can be removed by drying the zeolite at a temperature of from 240–250° C. at a pressure of from 0.1 –0.05 mm Hg for 4 hours. The zeolite may also contain additional water which requires higher temperatures for removal. Although it is not possible to distinguish between water of hydration and absorbed water, for the purpose of this invention the residual water content of the zeolites which is not removed by the 240–250° C. drying procedure is considered to be water of hydration. The complete removal of this residual water might further improve the shape selectivity function of the zeolite. However, the presence of the residual water does not prevent the achievement of good yields and selectivity when using much smaller amounts of catalyst than are required by the prior art process. It is important that the dried zeolites be protected against excessive exposure to atmospheric moisture prior to use, because the zeolites may pick up sufficient moisture during handling, or even when kept in a desiccator for a few days, so as to significantly decrease their effectiveness.

Zeolites as received from vendors may contain varying amounts of absorbed water. The HY zeolite (390HUA) used in the examples presented hereinafter was heated at a temperature of 240–250° C. for four hours at a reduced pressure of from 0.1 to 0.05 mm Hg to ensure that absorbed water was removed therefrom. Thermogravimetric analysis (TGA) under nitrogen over the range of from 20–900° C. removes not only the absorbed water, but also the water of hydration. Although such high temperature drying conditions can be used, the foregoing drying procedure at 240–250° C. and reduced pressure is sufficient to provide zeolite HY or HMor capable of achieving good yields and selectivity when used with a Lewis acid in accordance with this invention. HY zeolite is the most preferred zeolite for use in the practice of this invention.

The amount of zeolite catalyst used is preferably selected to give the best yield and selectivity for any particular catalyst combination and aromatic substrate to be brominated. A minimum amount of at least about 1 gram of HY zeolite per mole of substrate, and preferably a minimum amount of at least about 2 grams of HY zeolite per mole of substrate should be used in order to obtain substantially complete conversions with good selectivity. For economic reasons, the amount of zeolite should be kept to the minimum consistent with good yields and selectivity. In most cases, good yields and selectivity can be obtained using less than 10 grams of HY or HMor zeolite per mole of substrate. Preferred proportions are in the range of 2 to 6 grams of HY or HMor zeolite per mole of aromatic substrate.

Lewis Acid

The other component of the catalyst combinations utilized in the practice of this invention is a Lewis acid. While various Lewis acids such as aluminum chloride, aluminum bromide, stannic chloride, zinc chloride, cupric chloride, iron powder, zinc, etc., can be used, the most preferred Lewis acids because of the excellent performance achieved therewith are ferric halides, such as ferric bromide, and particularly ferric chloride. Typically the Lewis acid is employed in an amount such that per each part by weight of zeolite HY used or HMor, there is in the range of 0.005 to 0.5 part by weight, and preferably in the range of 0.01 to 0.25 part by weight, of Lewis acid.

Aromatic Substrates

The aromatic substrates which can be selectively brominated by the process of the invention include polycyclic aromatic compounds such as naphthalene, indene, and tetrahydronaphthalene, as well as benzene compounds. The invention is particularly useful in the para-bromination of benzene derivatives. Non-limiting examples of such derivatives include $C_1$ to $C_{10}$ (preferably $C_1$ to $C_4$) monoalkyl substituted arenes or monohaloarenes such as toluene, ethylbenzene, cumene, propylbenzene, butylbenzene, isobutylbenzene, tert-butylbenzene, fluorobenzene, chlorobenzene, bromobenzene, and the like.

Brominating Agent

Any agent that is capable of producing electrophilic bromonium ion ($Br^+$) can be used in the bromination process. Examples of such agents include bromine ($Br_2$), N-bromosuccinimide (NBS), dibromodimethyl hydantoin and BrCl. Of these, bromine is most preferred as its use is more economical, and its use simplifies product workup, product recovery, and waste product disposal operations. Indeed, essentially the only co-product formed when using bromine is hydrogen bromide which is a very useful co-product for various chemical syntheses. It is preferred that when bromine is used in the process of this invention, it is essentially anhydrous, i.e., it contains, if any, less than 100 ppm by weight of water, and no more than 10 ppm by weight of organic impurities, e.g., oil, grease, carbonyl-containing hydrocarbons, metal, and the like. With such a bromine purity, there is little, if any, adverse impact on the color attributes of the products. Available, commercial grade bromine may have such purity. If, however, such is not available, the organic impurities and water content of the bromine can be conveniently reduced by mixing together a 3 to 1 volume ratio of bromine and concentrated (94–98 percent) sulfuric acid. A two-phase mix is formed which is stirred for 10–16 hours. After stirring and settling, the sulfuric acid phase, along with the impurities and water, is separated from the bromine phase. To further enhance the purity of the bromine, the recovered bromine phase can be subjected to distillation.

Process Operations

The ar-bromination process is typically performed as a slurry process, and can be carried out in bulk when brominating a liquid aromatic substrate, which thus provides a liquid phase for the reaction. Such mode of reaction is preferred. However, an ancillary organic diluent can be included in such liquid medium if desired, and when the aromatic substrate is a solid at the bromination temperature, an ancillary organic diluent or mixture of diluents is used. Organic diluent(s) used for the bromination process should be anhydrous and inert to the reactants. In addition, the diluent should be capable of forming a homogeneous solution with the aromatic substrate, especially when the latter is a solid at the selected bromination temperature(s). Preferred diluents include acetonitrile, propionitrile and halogenated, saturated aliphatic hydrocarbons such as lower alkyl halides—for example, carbon tetrachloride, chloroform, sym-tetrachlorethane, bromochloromethane, methylene chloride, 1,1,2-trichloroethane, 1,2-dibromoethane, dibromomethane, ethylene dichloride, and the like. Liquid saturated hydrocarbon diluents are also suitable, and are typified by such materials as, for example, cyclohexane, methylcyclohexane, 1,3-dimethylcyclohexane, 1,4-dimethylcyclohexane, isopropylcyclohexane, and p-menthane.

The reactants can be employed in any proportions equivalent to up to 1–1.1 mole of bromine ($Br_2$) per mole of the substrate. Where there is an excess of the substrate the excess can serve as a diluent, and the brominating agent is the limiting reactant in forming the monobrominated product. Preferably bromine and the aromatic substrate are employed in substantially equimolar amounts (e.g., 0.95 to 1.05 moles of bromine per mole of aromatic substrate), although it is possible to use a higher molar ratio of bromine to substrate if some overbromination can be tolerated.

If and when used, amounts of diluent are typically employed that provide a concentration of from 10 to 100 parts by weight of solvent per part by weight of aromatic substrate. The amount of brominating agent used is preferably in slight excess (e.g., 5 to 10%) over the stoichiometric amount needed to substitute a single bromine atom onto the aromatic ring. The order of addition of reactants can be varied.

In the practice of this invention, reaction temperatures are maintained in the range of from 30 to 70° C. and preferably in the range of 35 to 60° C. for substantially the entire reaction period, i.e. at least until all of the bromine and aromatic substrate have been mixed together. Most preferably the reaction temperature is maintained in the range of 35 to 50° C. throughout most, if not all, of the period during which bromination is occurring. The bromination reaction is exothermic. Therefore, temperature control is preferably maintained by portionwise addition of bromine to the aromatic substrate, such addition being carried out continuously or in spaced-apart increments. Surprisingly, even when adding bromine to fluorobenzene at temperatures in the range of 35–50° C., the reaction is highly selective. Moreover, as shown by Comparative Example B hereinafter, at 0° C., no reaction occurred, and little if any reaction occurred at room temperature. Thus the aromatic substrate and a portion of the bromine and the catalyst components can be charged to the reactor at room temperature and then sufficient heat added to initiate the exothermic bromination. Alternatively, the catalyst components and aromatic substrate can be mixed together and preheated to a bromination initiation temperature and then the bromine addition can be initiated. The reactions are usually complete in from 1 to 4 hours, and can be completed, at least in some cases, in two hours or less. Preferably, the reaction is performed at least predominately at one reaction temperature in the range of 30 to 50° C., or at least predominately at two or more different reaction temperatures in the range of 30 to 50° C. at different times during the reaction, which times may be, but need not be, consecutive. It is also possible to have different portions of the reaction mixture at different temperatures within the range of 30 to 70° C. at the same time. Therefore in ordinary, plain English, the reaction can be conducted at one or more reaction temperatures in the range of 30 to 70° C. After the bromination reaction is complete, the product can be recovered and purified, if necessary, using conventional techniques. For example, the zeolite and Lewis acid components can be separated by filtration and the filtrate is washed with a 20% by weight solution of aqueous sodium sulfite and then dried either by azeotropic distillation or by the use of a drying agent such as magnesium sulfate. Alternatively, the reaction mixture may be distilled at the end of the reaction in order to recover the desired product, and leaving the zeolite as, or in, the distillation bottoms. Fresh aromatic substrate for selective ar-bromination (e.g., fluorobenzene) can then be recharged to the reactor, and bromination can again be conducted in the same reactor. Such procedure can be carried out successively until the activity of catalyst is diminished, at which point it is replaced with fresh suitably active catalyst components.

Other methods of temperature control that can be used include reflux cooling in a reaction mass that will under reflux at a suitable temperature, or use of cooling water or other heat exchange liquid. However, as indicated above, there is no need for utilizing refrigeration, with all of its attendant capital and operating costs.

The invention is further illustrated by, but is not intended to be limited to, the following example.

EXAMPLE

Bromination of Fluorobenzene in the Presence of HY Zeolite and Ferric Chloride

HY zeolite (390HUA; TOSOH USA, Inc.) was dried at 240–250° C. at a pressure of from 0.1–0.05 mm Hg for 4 hours. Fluorobenzene (56.2 grams, 0.59 mole) was added to a mixture of 2 grams of the freshly dried HY zeolite and 0.22 gram of the ferric chloride. The resulting slurry was stirred under nitrogen at about 35° C. for about 15 minutes. Bromine (47 grams, 0.29 mole) was added portionwize over a period of 0.5 hour, and the HBr co-product was continuously purged and scrubbed in an aqueous sodium hydroxide solution. The exothermic reaction raised the temperature to 48–50° C. Gas chromatographic (GC) analysis of a sample of the reaction mixture showed that it contained 50% of fluorobenzene, 1% of o-bromofluorobenzene, and 49% of p-bromofluorobenzene. More bromine (47 grams, 0.29 mole) was added at a rate that maintained the temperature below 50° C. The bromine addition was completed in 20 minutes, and the reaction mixture was stirred for another 40 minutes at 45–47° C., thereby providing a total reaction time of 1.5 hours. GC analysis of a sample of this reaction mixture showed complete conversion of fluorobenzene to p-bromo-fluorobenzene (97%), o-bromofluorobenzene (2%), and traces of unidentified heavier components (1%). The para/ortho ratio of the product was 98/2.

Comparative Example A

Bromination of Fluorobenzene in the Presence of HY Zeolite

HY zeolite (390HUA; Tosoh USA Co.) dried at 240–250° C. at a pressure of from 0.1 –0.05 mm Hg for 4 hours was used as the sole catalyst component. Fluorobenzene (56.2 grams, 0.59 mole) was added to 2 grams of the freshly dried HY zeolite and stirred under nitrogen at room temperature for about 15 minutes. Bromine (94 grams, 0.59 mole) was added portionwize over a short period of time, and the co-product was continuously purged and scrubbed in an aqueous sodium hydroxide solution. An exothermic reaction ensued, and the reaction mixture was stirred for 24 hours. Gas chromatographic (GC) analysis of a sample of the reaction mixture taken at the end of the 24-hour period showed that it contained 61% of fluorobenzene, and 39% of monobromofluorobenzenes. The para/ortho ratio in the product was 98/2.

The following Table summarizes the results of additional comparative experiments which were conducted under the same conditions and with the same proportions except as indicated in the Table. These results further demonstrate the advantages of this invention from the standpoints of achieving high yields of desired product with high selectivities in short reaction times. The aromatic substrate used was fluorobenzene, and the zeolite used was an HY zeolite from Tosoh USA, Inc. namely 390HUA.

TABLE

COMPARATIVE EXPERIMENTS

| Reagents Used | Method not of this Invention | Method not of this Invention | Method of this Invention |
|---|---|---|---|
| FeCl₃ | ~0.4 wt % | None | 0.4 wt % |
| Zeolite | None | 4 wt % | 4 wt % |
| Time for Total Conversion | >24 hrs | 20–24 hrs | 2–4 hrs |
| Bromine | Neat | Neat | Neat |
| HBr | Purged | Purged | Purged |
| p/o ratio | 90/10 | 98/2 | 98/2 |

Comparative Example B

Attempted Bromination of Fluorobenzene in the Presence of HY Zeolite and Ferric Chloride at Low Temperatures While keeping the temperature at 0 to 2° C., bromine (47 grams, 0.29 mole) was added to and stirred with fluorobenzene (56 grams, 0.58 mole) in the presence of zeolite 390HUA (2 grams) and ferric chloride (0.22 gram). No bromination was detected. Warming the mixture to room temperature caused very little change—essentially no perceptible reaction occurred.

The materials referred to by chemical name or formula anywhere in the specification or claims hereof are identified as ingredients to be brought together in connection with performing a desired operation or in forming a mixture to be used in conducting a desired operation. Accordingly, even though the claims hereinafter may refer to substances in the present tense (e.g., "comprises" or "is"), the reference is to the substance, as it existed at the time just before it was first contacted, blended or mixed with one or more other substances in accordance with the present disclosure. The fact that a substance may lose its original identity through a chemical reaction, complex formation, solvation, ionization, or other transformation during the course of contacting, blending or mixing operations, if done in accordance with the disclosure hereof and with the use of ordinary skill of a chemist and common sense, is within the purview and scope of this invention.

Numerical ranges given herein are not intended to be absolute limits since as in virtually any chemical reaction slight changes rarely materially change the results obtained.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims.

What is claimed is:

1. A process for ar-brominating an ar-brominatable aromatic substrate, said process comprising reacting said substrate with a brominating agent in a liquid reaction medium at a bromination temperature in the range of 30 to 70° C. and in the presence of a catalyst composition formed by including in said medium a combination of (i) a shape selective HY or HMor zeolite catalyst, and (ii) at least one Lewis acid in a ratio of from 0.005 to 0.5 part by weight of (ii) per part by weight of (i), the amount of said zeolite being no more than about 10 grams per mole of aromatic substrate.

2. A process according to claim 1 wherein said Lewis acid is a ferric halide.

3. A process according to claim 1 wherein said Lewis acid is ferric chloride.

4. A process according to claim 1 wherein said brominating agent is bromine.

5. A process according to claim 1 wherein the bromination temperature is in the range of 30 to 60° C., and wherein the amount of said zeolite is in the range of 1 to 10 grams per mole of aromatic substrate.

6. A process according to claim 1 wherein said zeolite catalyst has an average pore size in the range of 6 to 8 angstroms, said substrate is a mono-substituted benzene compound, said brominating agent is bromine, and the principal product formed in said process is a para-brominated benzene compound.

7. A process according to claim 6 wherein said Lewis acid is a ferric halide, wherein the bromination temperature is in the range of 30 to 60° C., and wherein the amount of said zeolite is in the range of 1 to 10 grams per mole of said substrate.

8. A process according to claim 7 wherein said Lewis acid is ferric chloride, and wherein the bromination temperature is in the range of 30 to 50° C.

9. A process according to claim 6 wherein said average pore size is in the range of 6 to 8 angstroms, wherein said substrate is toluene, ethylbenzene, n-propylbenzene, n-butylbenzene fluorobenzene, chlorobenzene, or bromobenzene, and wherein the bromination temperature is in the range of 30 to 60° C.

10. A process according to claim 6 wherein said substrate is fluorobenzene.

11. A process according to claim 6 wherein the reaction is performed at least predominately at one reaction temperature in the range of 30 to 50° C., or at least predominately at two or more different reaction temperatures in the range of 30 to 50° C. at different times during the reaction, which times may be, but need not be, consecutive.

12. A process according to claim 11 wherein:
   a) said Lewis acid is ferric chloride;
   b) said average pore size is in the range of 6.5 to 7.5 angstroms; and
   c) said substrate is toluene, ethylbenzene, n-propylbenzene, n-butylbenzene, fluorobenzene, chlorobenzene, or bromobenzene.

13. A process according to claim 12 wherein said substrate is fluorobenzene.

14. A process for ar-brominating an ar-brominatable aromatic substrate, said process comprising reacting said substrate with bromine in a liquid reaction medium at a bromination temperature in the range of 30 to 70° C. and in the presence of a catalyst composition formed by including in said medium a combination of (i) a shape selective HY zeolite catalyst, and (ii) at least one Lewis acid in a ratio of from 0.005 to 0.5 part by weight of (ii) per pair by weight of (i), the amount of said zeolite being in the range of 2 to 6 grams per mole of aromatic substrate.

15. A process according to claim 14 wherein said zeolite catalyst has an average pore size in the range of 6 to 8 angstroms, said substrate is a mono-substituted benzene compound, and wherein said Lewis acid is a ferric halide.

16. A process according to claim 15 wherein said Lewis acid is ferric chloride.

17. A process according to claim 15 wherein said average pore size is in the range of 6.5 to 7.5 angstroms, and said substrate is fluorobenzene.

18. A process according to claim 15 wherein the reaction is performed at least predominately at one or more temperatures in the range of 30 to 60° C.

19. A process according to claim 15 wherein:

a) said Lewis acid is ferric chloride;

b) said average pore size is in the range of 6.5 to 7.5 angstroms;

c) said substrate is toluene, ethylbenzene, n-propylbenzene, n-butylbenzene, fluorobenzene, chlorobenzene, or bromobenzene; and d) said bromination temperature is in the range of 30 to 60° C.

20. A process according to claim 19 wherein said substrate is fluorobenzene, and wherein said bromination temperature is in the range of 30 to 50° C.

* * * * *